United States Patent [19]

Pothapragada et al.

[11] Patent Number: 5,300,714
[45] Date of Patent: Apr. 5, 1994

[54] METHOD OF PURIFYING SATURATED FLUOROPERHALOCARBON LIQUIDS

[75] Inventors: Venkateswarlu Pothapragada, St. Paul; Donald F. Hagen, Woodbury; Robert B. Fletcher, St. Paul; Frederick E. Behr, Woodbury, all of Minn.

[73] Assignee: Minnesota Mining and Manufacturing Company, St. Paul, Minn.

[21] Appl. No.: 685,813

[22] Filed: Apr. 15, 1991

Related U.S. Application Data

[63] Continuation-in-part of Ser. No. 525,976, May 18, 1990, abandoned.

[51] Int. Cl.$^5$ ............................................. B01D 15/00
[52] U.S. Cl. .................................. 570/179; 210/679; 210/690
[58] Field of Search ................. 210/660, 679, 690; 570/179

[56] References Cited

U.S. PATENT DOCUMENTS

| | | | |
|---|---|---|---|
| 2,863,830 | 12/1958 | Schneider et al. | 570/179 |
| 2,879,228 | 3/1959 | Holeton | 570/179 |
| 3,696,156 | 10/1972 | Weeks | 260/648 F |
| 3,876,394 | 4/1975 | Nix | 55/77 |
| 4,211,658 | 7/1980 | McDonald et al. | 210/198.2 |
| 4,755,293 | 7/1988 | Sakamoto et al. | 210/198.2 |
| 4,766,261 | 8/1988 | Bierl | 570/179 |
| 4,842,746 | 6/1989 | Fowler et al. | 210/690 |

FOREIGN PATENT DOCUMENTS

| | | |
|---|---|---|
| 0370688 | 5/1990 | European Pat. Off. .......... 570/179 |
| 160718 | 2/1984 | Fed. Rep. of Germany . |
| WO90/10612 | 9/1990 | PCT Int'l Appl. . |

OTHER PUBLICATIONS

Ullmanns Encyclopedia of The Technical Chemistry, Third Completely Revised Edition, vol. 2/1 Application of Physical and Physico-Chemical Methods in the Laboratory, 1961.

Turbini, L. J., Zado, F. M., "Chemical and Environmental Aspects of Condensation Reflow Soldering", Electronic Packaging and Production, vol. 20 (1980).

Smith, L. W., Gardener, R. J., and Kennedy, G. L., Jr., "Short Term Inhalation Toxicity of Perfluoroisobutylene", Drug and Chemical Toxicology, vol. 5 (1982) pp. 295–303.

An English translation of Danishevskii, S. L., and Kochanov, M. M., "Toxicity of Some Fluoro-Organic Compounds", Oigiena Truds i Professional'aye Zebeleveniay, vol. 5, (1961).

Waritz, R. S., and Kwon, B. K., "The Inhalation Toxicity of Pyrolysis Products of Polytetrafluoroethylene Heated Below 500 Degrees Centigrade", American Industrial Hygiene Association Journal, vol. 29, (1968).

"Fluorinert TM Liquids", 3M Publication No. 98-02-11-441-2(78.2)RI.XY.

U.S. Defensive Publication T983,009 (Treat).

*Primary Examiner*—Ivars Cintins
*Attorney, Agent, or Firm*—Gary L. Griswold; Walter N. Kirn; Eloise J. Maki

[57] ABSTRACT

A method of removing olefinic impurity, such as perfluoroisobutylene, from fluoroperhalocarbon liquid, such as perfluorinated liquid, comprising the step of contacting the fluoroperhalocarbon liquid with a body of particles comprising particles selected from the group consisting of alumina, alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof.

18 Claims, 1 Drawing Sheet

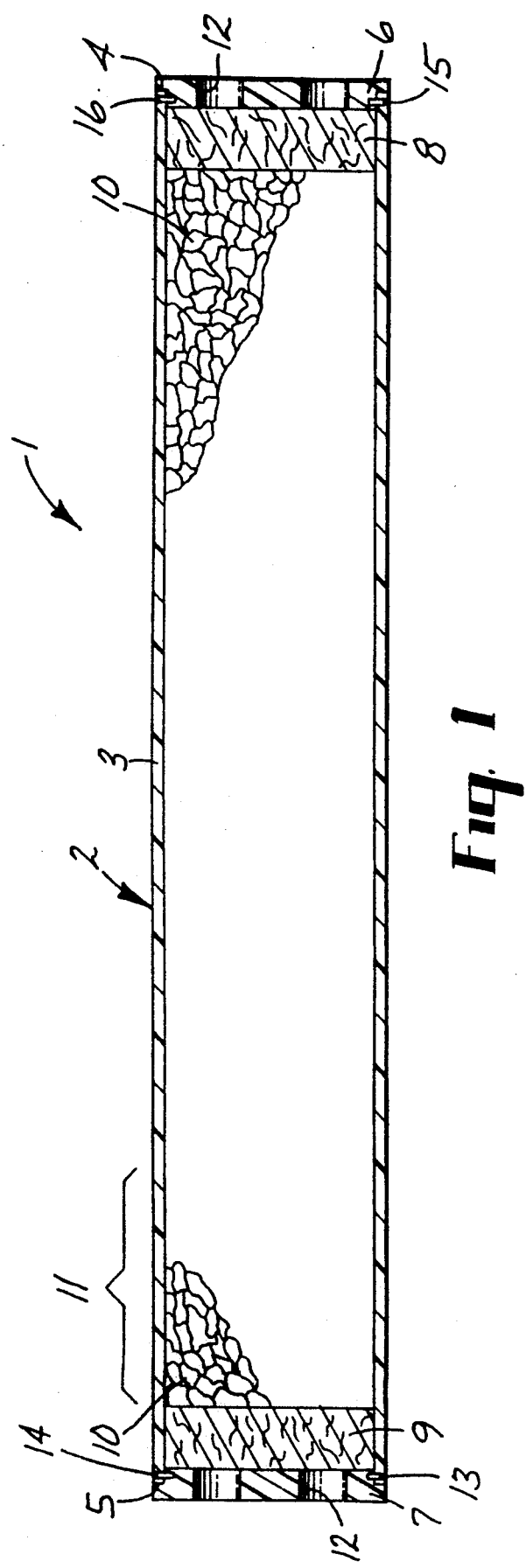
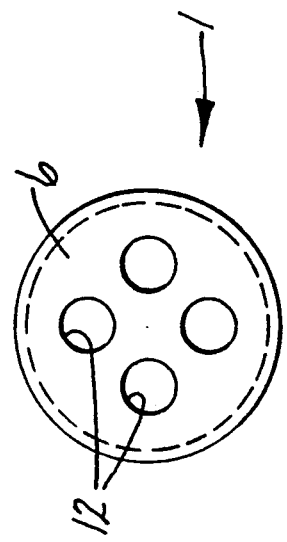
Fig. 1
Fig. 2

METHOD OF PURIFYING SATURATED FLUOROPERHALOCARBON LIQUIDS

This is a Continuation-in-Part application of U.S. Ser. No. 07/525,976 filed on May 18, 1990, now abandoned.

FIELD OF THE INVENTION

This invention relates to a method of removing olefinic impurities comprising perfluoroolefins and perfluorochloroolefins from saturated fluoroperhalocarbon.

BACKGROUND

Fluoroperhalocarbon liquids (e.g., perfluorinated liquids) have many industrial uses, such as coolants for electronic devices (e.g., supercomputers) and as heat transfer media in vapor-phase soldering processes. However, upon heating many of these liquids at high temperatures, toxic impurities such as certain perfluoroolefins and perfluorochloroolefins may form. These impurities may be hazardous to persons handling the liquid or operating equipment containing the contaminated liquid.

For example, perfluoroisobutylene (hereinafter, for brevity referred to as PFIB) is a colorless gas at room temperature and is widely recognized as a toxic material, Exposure of persons to even low concentrations of PFIB may be lethal (e.g., Turbini, L. J., Zado, F. M., "Chemical and Environmental Aspects of Condensation Reflow Soldering", *Electronic Packaging and Production*, Vol. 20 (1980), Smith, L. W., Gardener, R. J., and Kennedy, G. L. Jr., "Short Term Inhalation Toxicity of Perfluoroisobutylene", *Drug and Chemical Toxicology*, Vol. 5, (1982) pp. 295-303, Danishevskii, S. L., and Kochanov, M. M., "Toxicity of Some Fluoro-Organic Compounds", *Oigiena Truds i Professional'aye Zebeleveniay*, vol. 5, (1961) and Waritz, R. S., and Kwon, B. K., "The Inhalation Toxicity of Pyrolysis Products of Polytetrafluoroethylene Heated Below 500 Degrees Centigrade", *American Industrial Hygiene Association Journal*, Vol. 29 (1968).

Various methods have been suggested for reducing the hazard of PFIB exposure of operators of equipment that produce PFIB (Turbini, L. J., Zado, F. M., "Chemical and Environmental Aspects of Condensation Reflow Soldering", *Electronic Packaging and Production*, Vol. 20 (1980), "Fluorinert TM Liquids", 3M Publication No. 98-0211-4411-2(78.2)R1 XY). Some of these methods include techniques of operating and maintaining vapor-phase soldering equipment to avoid superheating perfluorinated liquids, thus reducing the amount of PFIB produced, and standards of designing work areas to provide sufficient ventilation to maintain PFIB levels at less than hazardous levels. However, maintenance and operating techniques probably cannot completely prevent the formation of PFIB, and venting PFIB to the atmosphere is not environmentally desirable. U.S. Defensive Publication T983,009 (Treat) describes a method of converting PFIB in a mixture of fluorine-containing compounds into a nontoxic ether by contacting the mixture with a solution of methanol and a selected hydrogen halide. While this method does produce products which are generally less toxic than PFIB, it has disadvantages, including 1) being complex to operate in a continuous mode, since various feed streams of reactants must be controlled, 2) use of hazardous hydrogen halides (e.g., HF and HCl) as reactants and 3) yielding products which may create a disposal problem. U.S. Pat. No. 3,696,156 (Weeks) describes a method of removing perfluoroolefins and perfluorochloroolefin impurities from saturated fluoroperhalocarbon compounds having two to six carbon atoms, by contacting the impure fluoroperhalocarbon in the vapor phase at about 180° to 250° C. with alumina containing a basic alkali metal or alkaline earth metal hydroxide or oxide. One of the disadvantages of this process is that it requires handling hot gas contaminated with hazardous compounds.

Thus, it would be useful to develop a process to remove perfluoroolefin and perfluorochloroolefin impurities from fluoroperhalocarbon compounds that permitted purification of the compounds in their liquid state at lower temperatures.

SUMMARY OF THE INVENTION

In one aspect, the invention provides a method of removing olefinic impurity comprising, and preferably, consisting essentially of, compounds selected from the group consisting of perfluoroolefin (e.g., PFIB) and perfluorochloroolefin compounds and mixtures thereof, from fluoroperhalocarbon liquid (e.g., perfluorinated liquid), comprising the step of contacting the fluoroperhalocarbon liquid with a body of particles comprising, or preferably consisting essentially of, particles selected from the group consisting of alumina (preferably basic alumina), alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof. Optionally, all or at least some portion, generally a minor portion (i.e., no more than 50 weight percent), of the particles comprising the body of particles may be coated with a pH indicating composition (e.g. phenolphthalein), such that when the capacity of the body of particles to remove the aforementioned impurities is near exhaustion, the coated particles will change color.

In another aspect, this invention provides a cartridge useful for removing olefinic impurity from fluoroperhalocarbon liquid comprising:

a body of particles comprising, or preferably, consisting essentially of, particles selected from the group consisting of alumina (preferably basic alumina), alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof, and a housing to contain the body of particles, having walls, the housing having an external and an internal surface and at least two openings communicating between the external and internal surfaces which can serve as inlet and outlet ports for the fluoroperhalocarbon liquid.

In yet another aspect, this invention provides a cartridge comprising the body of particles having some portion of the particles coated with pH indicating composition and a housing wherein said housing comprises:

A) a hollow tube, at least a portion of which comprising, and preferably consisting essentially of, light-transmitting material (e.g., acrylic plastic), permitting detection of a color change of the coated particles, having an inlet end and an outlet end, B) two end caps each having at least one opening, and preferably a plurality of openings, and C) two particle screens, wherein one end cap is attached to each end of the hollow tube, and together the tube and end caps form an enclosure around the body of particles, and one particle screen is located at each of the ends of the tube between the body of particles and the end cap.

One advantage of the instant invention is that it can be easily used to purify fluoroperhalocarbon liquids on either a batch or a continuous basis at ambient temperatures. Also, once the capacity of the body of particles to remove olefinic impurity has been consumed, the body of particles, in some cases, may be disposed of directly in a landfill because it is believed that the impurities may be irreversibly adsorbed on the body of particles or destroyed by chemical reaction with the body of particles. Another advantage of the instant invention is that the color change of the body of particles provides a convenient means for an operator to determine when to replace the cartridge.

BRIEF DESCRIPTION OF THE DRAWINGS

In the accompanying drawings, FIG. 1 is a cross-sectional view of one embodiment of the cartridge of this invention.

FIG. 2 is an end view of one embodiment of this invention.

DETAILED DESCRIPTION OF THE INVENTION

The fluoroperhalocarbon liquid useful in this invention comprises, or preferably consists essentially of, one or more normally liquid fluoroperhalocarbon compounds.

The fluoroperhalocarbon compounds contain no ethylenic unsaturation, consist of carbon, fluorine and optionally chlorine, nitrogen, oxygen or sulfur, and have at least 2 carbon atoms and preferably 4 to 18 carbon atoms. A representative class of the fluoroperhalocarbon compounds includes fluorinated linear, branched or cyclic alkanes, ethers, tertiary amines and aminoethers.

One class of fluoroperhalocarbon liquid preferably used in the practice in this invention is perfluorinated liquid. Many perfluorinated liquids are commercially available, such as, Fluorinert ™ Electronic Liquids and 3M ™ Condensation Heating Fluid, both available from the 3M Company, Krytox ™ liquids available from E.I. duPont de Nemours & Co., Flutec ™ PP liquids available from ISC Chemicals Limited, and Galden ™ HS liquids available from Montedison, Inc.

Representative fluoroperhalocarbon liquids useful in this invention include perfluoromethyldecalin, perfluorinated polyethers, perfluorotributylamine, perfluorodihexyl ether, perfluoroperhydrophenanthrene, perfluorotriamylamine, perfluorotrihexylamine, perfluorotriethylamine, perfluoro-4-methylmorpholine, perfluoro-2-ethyltetrahydrofuran, perfluorohexane, perfluoro-4-isopropylmorpholine, perfluorodibutylether, perfluorooctane, perfluorotripropylamine, perfluoromethylcyclohexane, 1,4-bis(pentafluorothio)perfluorobutane, $(C_3F_7)_2NCF_2CF_2CF_2N(C_3F_7)_2$, $(C_2F_5)_2NC_2F_4O(CF_2)_4OC_2F_4N(C_2F_5)_2$, $CCl_2F-CCl_2F$, perfluoropentane, perfluoroheptane, 1,3-bis(trifluoromethyl)perfluorocyclohexane, $C(CF_2OC_2F_5)_4$, $CF_2(OC_4F_9)_2$, and mixtures thereof.

The body of particles comprises particles selected from the group consisting of alumina (preferably basic alumina), alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof. The particles should have a pH of at least 4, preferably at least 6, and most preferably 7 or more. The pH can be determined by preparing a slurry of three grams of the particles in 50 mL of deionized water (having a pH of approximately 5.8 to 6.3), shaking the slurry for 30 minutes, transferring the slurry into a glass beaker containing a plastic-coated, magnetic stirring bar, placing a glass-calomel electrode in the slurry and allowing it to equilibrate for about 5 minutes while stirring at about 150 rpm, and after equilibration, measuring the pH.

Representative alkaline earth oxides and hydroxides, basic carbonates and basic phosphates include calcium hydroxide, calcium oxide, magnesium oxide, calcium phosphate tribasic, and magnesium carbonate (i.e., approximately $4MgCO_3.Mg(OH)_2.4H_2O$). Representative alkali metal oxides and hydroxides include sodium hydroxide, sodium oxide, potassium hydroxide and lithium hydroxide. A representative tin oxide is stannic oxide. Representative transition metal oxides include cerium(ic) oxide, chromic oxide and zirconium oxide.

The particles comprising the body of particles can have various forms (e.g., powders, granules, crystals, fibers and pellets), and can be of various sizes. Generally, a cartridge containing a body of particles having a very large surface area (e.g, one comprising a powder of alumina) will remove the olefinic impurity faster from a given feed stream than another body of the same weight which has less surface area (e.g., one comprising pellets); however, it will also result in a greater pressure drop across a cartridge. Thus, the selection of particle size and form is largely a function of system design factors, such as the desired cartridge pressure drop, dimensional constraints for the cartridge, desired flow rate and the concentration of olefinic impurity in the fluoroperhalocarbon liquid. One particularly useful form of the particles are granules which are 1 to 3 mm in diameter. These particles have been shown to result in very low pressure drops in cartridges similar in construction to the cartridge illustrated in FIG. 1. Activated alumina granules are particularly preferred because they provide high surface area without requiring small particle size.

Preferably, basic alumina is used in this invention because of its ready commercial availability in various particle sizes and its relatively high surface area and high capacity for absorbing olefinic impurities. Basic alumina particles generally comprise, or consist essentially of, $Al_2O_3$ particles coated with a solution or slurry of an alkali metal or alkaline earth hydroxide or oxide (e.g., sodium hydroxide, calcium oxide or magnesium hydroxide) which have been heated until they reach the desired activity level (typically between grades I to V and preferably grade I). Typically, commercially available basic alumina particles, such as those available commercially from Universal Scientific, Inc. may contain about 79 to 99 weight percent $Al_2O_3$, about 0.1 to 20 percent water, and may also contain a small amount of other metal oxides, such as $Na_2O$ and $Fe_2O_3$, as well as flow conditioners (e.g., $SiO_2$). Particularly useful alumina particles are essentially anhydrous (i.e., no more than 3 weight percent of water). Such particles can be purchased commercially, or they can be prepared by drying non-anhydrous particles. For example, Universal Scientific Inc.'s AL2100 basic alumina particles can be dried to an essentially anhydrous state by heating a shallow bed of particles in an oven at 180° C. for 3 hours.

The basic alumina particles should have a pH above 7, and preferably 8 to 12.

The particles coated with pH indicator can be prepared by first dissolving or dispersing a pH indicating compound (e.g., phenolphthalein) in an alcohol (e.g., methanol). Particles are then added to the alcohol solution or dispersion and the resulting mixture is stirred at ambient temperature until the pH indicating compound has been adsorbed or absorbed by the particles. The solid particles are then separated from the liquid, and are allowed to air dry. Preferably, the particles may be further dried by heating in an oven at 180° C. for 3 hours.

The olefinic impurity removed from fluoroperhalocarbon liquid according to the process of this invention comprises, and preferably consists essentially of, compounds selected from the group consisting of perfluoroolefinic and perfluorochloroolefinic compounds and mixtures thereof, wherein said compounds have at least one ethylenic unsaturation, two or more carbon atoms, and preferably about 2 to 6 carbon atoms. Representative examples of olefinic impurity include PFIB, hexafluorocyclobutene and perfluoro-2-butene.

The features and benefits of this invention can be more easily understood by reference to the cartridge depicted in FIG. 1 and 2.

FIG. 1 depicts a flow-through cartridge useful for the removal of olefinic impurity from fluoroperhalocarbon liquid on a continuous basis. It is particularly useful in applications where in-line purification is desirable. The cartridge 1 comprises a housing 2 comprising a hollow tube 3 having an inlet end 4 and an outlet end 5, two end caps 6,7 each having one or more openings 12 and two particle screens 8, 9 and a body of particles 10.

The body of particles substantially fills the entire internal volume of the tube. When filling the tube, it is generally desirable to shake or tap the tube gently while filling to ensure relatively even packing of the particles. However, even after packing, the body of particles will generally contain a large void area. In the embodiment depicted in FIG. 1, a portion of the bed, indicated by the bracketed area 11, is coated with phenolphthalein. When the capacity of the cartridge to remove olefinic impurity nears exhaustion, the color of the coated particles will change from bright pink to white, indicating that the cartridge should be replaced. Alternatively, all of the particles in the tube can be coated with phenolphthalein or, phenolphthalein-coated particles comprising an amount less than all of the particles in the tube, can be evenly distributed throughout the body of particles filling the tube.

The tube is made of material which will not chemically react with the bed material or fluoroperhalocarbon liquid, and which will withstand the temperature and pressure of the fluoroperhalocarbon liquid feed stream. Preferably, at least a portion of the tube will comprise a light-transmitting material, that is, a material that is transparent or translucent to light, permitting detection of a change (e.g., a color change) of the coated particles. The tube depicted in FIG. 1 consists essentially of light-transmitting material. Generally, light-transmitting materials are transparent or translucent to UV or visible light, and are acceptable if they have the necessary durability and inertness. Colorless acrylic plastic or glass is generally a very useful material for the flow-through style cartridge depicted in FIG. 1 because it permits visual determination of a color change of the coated particles.

The end caps 6, 7 seal the ends of the hollow tube and each cap must have at least one opening 12, and preferably a plurality of openings, to provide an inlet and outlet for fluid flow. A plurality of openings is generally preferable because they may result in a better distribution of flow across the cartridge. The number, size and area of openings is largely determined by the pressure drop desired across the cartridge. The end caps may be fastened to the tube using any commonly known means such as clamping, adhesive or by roll pins 13, 14, 15 and 16.

The particle screens 8, 9 are located between the end caps and the body of particles. Their function is to screen the inflow and outflow of fluid feed and to prevent the particles from being swept from the cartridge by the fluid flowing through the cartridge. The particle screens may be made of any material which is durable, which will not chemically react with the particles or fluoroperhalocarbon liquid and which will withstand the temperature and pressure of the fluoroperhalocarbon liquid feed stream. The openings in the screens should be small enough to prevent particles from being swept from the cartridge by the liquid stream flowing through the cartridge. However, the openings should be as large as possible to minimize the pressure drop across the cartridge. Non-woven plastic webs are particularly useful as particle screens. Commercially available Scotchbrite ™ pads cut to a shape and size approximately the same as that of the internal cross-section of the tube have proven to be very effective.

Another embodiment of the cartridge comprises a body, of particles, and a housing which is not designed for flow-through operation. Such a housing need not be as durable as one designed for flow-through operation because it will not be subjected to pressurized feed streams. Generally, it will be desirable for such a housing to have many openings, for example it may be made of a relatively fine plastic mesh, so that the fluoroperhalocarbon liquid can easily diffuse into the body of particles, the particles are retained by the housing, and an operator can easily determine when the particles coated with a pH indicating compound have changed color.

The fluoroperhalocarbon liquid feed stream enters the flow ports of the cartridge depicted in FIG. 1 at the inlet end of the tube 4 and exits the cartridge through the flow ports in the end cap located at the outlet end of the tube 5. Generally, the weight of particles required for the body of particles depends upon the concentration of olefinic impurity and the flow rate of the liquid feed stream. As discussed above, particle surface area can also effect the weight of particles required to satisfy a particular liquid flow rate and impurity concentration. Generally, in systems processing fluoroperhalocarbon liquids, approximately 102 g of basic alumina particles, in the form of granules about 1 to 3 mm in diameter, are required to remove 0.15 g of PFIB. Preferably, the method of this invention will remove at least 99 weight percent of olefinic impurity from the fluoroperhalocarbon liquid, more preferably at least 99.9 weight percent, and most preferably essentially all olefinic impurity present in the fluoroperhalocarbon liquid feed, that is, the fluoroperhalocarbon liquid, after passing through the body of particles should have a concentration of olefinic impurity of less than 0.5 ppm.

The following non-limiting examples are provided to further illustrate the invention.

EXAMPLE 1

A cartridge similar in construction to the cartridge depicted in FIGS. 1 and 2 was evaluated to determine its effectiveness at removing olefinic impurity from a stream of Fluorinert TM FC-74 liquid (a perfluorinated alkane available from 3M Company) which had been used to cool a computer.

The test cartridge was approximately 42 in. (107 cm) long and had a 4 in. (10 cm) internal diameter. The cartridge contained about 12 (5.5 kg) pounds of basic alumina particles (AL 2100). About one half of the alumina particles in the cartridge had been coated with phenolphthalein.

The phenolphthalein-coated particles were prepared by mixing 6.8 L of methanol and 2.8 g of solid phenolphthalein. The particles (12 lbs.) were added to the methanol-phenolphthalein mixture which was then stirred until the particles were uniformly coated, the liquid was decanted and the coated particles were then allowed to air dry. After air drying, the coated particles were heated in an oven at 180° C. for 3 hours.

The uncoated alumina particles were also heated in an oven at 180° C. for 3 hours. The coated and uncoated particles were then blended and poured into the cartridge.

A feed stream of the PFIB-contaminated FC-74 was then fed to the cartridge at a flow rate of 2.56 GPM (10.2 L/min) from a 75 gallon reservoir which was continuously stirred. Pressure drop was measured across the cartridge and it was less than 10 psig (69 kPa).

Periodically, samples (60 mL) were taken from the reservoir and each was stored in a closed vial and allowed to equilibrate at room temperature. A sample of the head space gas from each of the sample vials was analyzed by gas chromatography to determine the concentration of PFIB gas. The concentration of PFIB is indicative of the cartridge's effectiveness at removing olefinic impurities. The quantity of PFIB remaining in the 75 gallons (284 L) liquid was then calculated by multiplying the headspace concentration by 50.

Two consecutive experiments were run on 75 gallon quantities of FC-74. Color change of the bright pink particles was determined by visual comparison to a standard vial containing a sample of the particles used to fill the tube. The PFIB concentrations in the headspace, the total quantity of PFIB remaining in the liquid feed and color change, if any, observed in the cartridge are summarized in Tables 1 and 2.

TABLE 1

| | EXPERIMENT 1 | | |
|---|---|---|---|
| Time (hours) | PFIB conc. in headspace (ppb v/v) | Total PFIB liq. (g) | Color change |
| 0 | 8000 | 1.08 | — |
| 0.5 | 4180 | 0.564 | none |
| 1.0 | 1800 | 0.230 | none |
| 1.5 | 1160 | 0.156 | none |
| 2.0 | 230 | 0.031 | none |

TABLE 2

| | EXPERIMENT 2 | | |
|---|---|---|---|
| Time (hours) | PFIB conc. in headspace (ppb v/v) | Total PFIB liq. (g) | Color change |
| 0 | 4620 | 0.62 | — |
| 0.25 | 3850 | 0.52 | none |
| 0.5 | 2460 | 0.33 | none |
| 0.75 | 1760 | 0.24 | none |
| 1.0 | 660 | 0.089 | none |
| 1.25 | 480 | 0.065 | none |
| 1.5 | 390 | 0.053 | none |
| 1.75 | 300 | 0.041 | none |
| 2.0 | 220 | 0.030 | none |

The data show that a cartridge containing activated basic alumina particles is not only very effective at removing PFIB as well as other olefinic impurities, from fluoroperhalocarbon liquids, but also that a cartridge of this size has a long operating life.

EXAMPLES 2-19 and COMPARATIVE EXAMPLES C1-C5

The following Examples illustrate the usefulness of various materials for removal of olefinic impurity from fluoroperhalocarbon liquid.

Into small glass vial, 0.1 g of each of the materials listed in Table 3 were added to 1.0 mL of FC-74 containing 975 ppm of PFIB. The vials were closed using caps having rubber diaphragms, and shaken for 30 minutes at ambient conditions before centrifuging. A sample of the vapor in the headspace above the liquid was then removed from each vial by puncturing the rubber diaphragm using a syringe needle and withdrawing the vapor sample. The vapor sample was immediately injected into a gas chromatographic column and peak area (if any) corresponding to PFIB was measured and compared to the results obtained from the analysis of a vapor sample from a control vial containing only the PFIB-contaminated-FC-74. The percent PFIB removal values given in Table 3 are calculated by taking the difference between GC PFIB peak areas of the control and treated samples, dividing the difference by the control sample's PFIB peak area and multiplying by one hundred.

TABLE 3

| Ex. | Particle | % PFIB Removal |
|---|---|---|
| 2 | Aluminum oxide (basic, AL2100) | 100 |
| 3 | Aluminum oxide (neutral) | 100 |
| 4 | Aluminum oxide (acidic) | 100 |
| 5 | Calcium hydroxide | 100 |
| 6 | Calcium oxide | 100 |
| 7 | Cerium(ic) oxide | 99 |
| 8 | Chromium oxide | 93 |
| 9 | Magnesium oxide | 100 |
| 10 | Silica gel | 63 |
| 11 | Stannic oxide | 100 |
| 12 | Zinc oxide | 100 |
| 13 | Zirconium oxide | 100 |
| 14 | Zirconium oxide (carbon coated) | 100 |
| 15 | Calcium phosphate, tribasic[1] | 66 |
| 16 | Calcium aluminum silicate[2] | 33 |
| 17 | Sodium aluminum silicate[3] | 49 |
| 18 | Blend of silica gel and zirconium oxide 1:1 by wt. | 91 |
| 19 | Magnesium carbonate[4] | 100 |
| C1 | Calcium carbonate | 0 |
| C2 | Calcium chloride | 0 |
| C3 | Magnesium sulfate | 0 |
| C4 | Cupric oxide | 0 |

TABLE 3-continued

| Ex. | Particle | % PFIB Removal |
|---|---|---|
| C5 | Vanadium pentoxide | 0 |

[1] $Ca_{10}(OH)_2(PO_4)_6$
[2] Molecular sieve 5A
[3] Molecular Sieve 13X
[4] $4MgCO_3 \cdot Mg(OH)_2 \cdot 4H_2O$ (approximately)

The data illustrates that not all of the particles are equally effective at removing olefinic impurity from fluoroperhalocarbon liquid. While those particles with the highest % PFIB removal values are probably better for use in this invention than those with lower values, the concentration of PFIB in the FC-74 liquid used in these Examples is much higher than that which would generally be encountered in contaminated fluoroperhalocarbon liquids. Thus, even those particles with lower % PFIB removal values are useful in this invention.

EXAMPLES 20-29

The following Examples illustrate what is believed to be the destruction of olefinic impurity by chemical reaction between impurity and the particles comprising the body of particles.

To small vials, 0.1 g of the compounds listed in Table 4 were added to 1 mL FC-74 containing 975 ppm of PFIB. The vials were closed and shaken for 30 minutes at ambient conditions before centrifuging. The particles were then recovered from the vials and were analyzed for the presence of fluoride ion. The amount of fluoride ion present in the particles themselves was also measured. The difference between the fluoride ion concentration of the treated particles versus the fluoride concentration of untreated particles is presented as "Excess fluoride ion" in Table 4.

TABLE 4

| Ex. | Particle | Excess fluoride ion (ppm) |
|---|---|---|
| 20 | Calcium hydroxide | 8.4 |
| 21 | Calcium phosphate, tribasic[1] | 3.4 |
| 22 | Magnesium carbonate[2] | 4.8 |
| 23 | Cerium(ic) oxide | 1.9 |
| 24 | Chromium oxide | 2.1 |
| 25 | Tin oxide | 2.7 |
| 26 | Zinc oxide | 4.9 |
| 27 | Zirconium oxide | 12.0 |
| 28 | Silica gel | 3.0 |
| 29 | Basic aluminum oxide[3] | 2.0 and 50 |

[1] $Ca_{10}(OH)_2(PO_4)_6$
[2] $4MgCO_3 \cdot Mg(OH)_2 \cdot 4H_2O$ (approximately)
[3] Measurements made on two different lots of AL2100 activated basic alumina.

An excess of fluoride ion is believed to be indicative of the destruction of olefinic impurity, in this instance PFIB, by chemical reaction between the impurity and the particles.

The data (Example 29) also illustrates the variation possible from lot to lot of basic alumina particles. Thus, it is important to control the activity grade level of the basic alumina particles and the type and amount of alkali metal or alkaline earth oxide or hydroxide coating on the alumina particles.

Various modifications and alterations of this invention will become apparent to those skilled in the art without departing from the scope and spirit of this invention, and it should be understood that this invention is not limited to the illustrative embodiments set forth herein.

We claim:

1. A method of removing olefinic impurity, wherein said olefinic impurity comprises perfluoroolefin or perfluorochloroolefin compounds or mixtures thereof, from fluoroperhalocarbon liquid comprising the step of contacting the fluoroperhalocarbon liquid with a body of particles comprising particles selected from the group consisting of alumina, alkali metal oxide, alkali metal hydroxide, alkaline earth oxide, alkaline earth hydroxide, silicon oxide, tin oxide, zinc oxide, alkaline earth basic carbonate, and alkaline earth basic phosphate particles and mixtures thereof.

2. A method according to claim 1 wherein the olefinic impurity consists essentially of compounds selected from the group consisting of perfluoroolefin and perfluorochloroolefin compounds and mixtures thereof.

3. A method according to claim 1 wherein the perfluoroolefin and perfluorochloroolefin have about 2 to 6 carbon atoms.

4. A method according to claim 1 wherein the olefinic impurity is perfluoroisobutylene.

5. A method according to claim 1 wherein the fluoroperhalocarbon liquid is perfluorinated liquid.

6. A method according to claim 1 wherein the body of particles comprises particles of basic alumina.

7. A method according to claim 6 wherein the activity grade of said body of particles is I to V.

8. A method according to claim 6 wherein the particles comprising the body of particles are essentially anhydrous.

9. A method according to claim 1 wherein the body of particles comprises particles of alkali metal oxide.

10. A method according to claim 1 wherein the body of particles comprises particles of alkali metal hydroxide.

11. A method of removing olefinic impurity from fluoroperhalocarbon liquid comprising the step of contacting the fluoroperhalocarbon liquid with a body of particles comprising particles selected from the group consisting of alumina, alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof, wherein at least some portion of the particles comprising said body of particles is coated with a pH indicating composition.

12. A method according to claim 11 wherein the pH indicating composition is phenolphthalein.

13. A method according to claim 11 wherein the olefinic impurity comprises compounds selected from the group consisting of perfluoroolefin and perfluorochloroolefin compounds and mixtures thereof.

14. A method according to claim 13 wherein the perfluoroolefin and perfluorochloroolefin have about 2 to 6 carbon atoms.

15. A method according to claim 13 wherein the olefinic impurity is perfluoroisobutylene.

16. A method according to claim 11 wherein the olefinic impurity consists essentially of compounds selected from the group consisting of perfluoroolefin and perfluorochloroolefin compounds and mixtures thereof.

17. A method according to claim 11 wherein the fluoroperhalocarbon liquid is perfluorinated liquid.

18. A method of removing olefinic impurity, wherein said olefinic impurity comprises perfluoroolefin or perfluorochloroolefin compounds or mixtures thereof from fluoroperhalocarbon liquid consisting of the steps of:

(a) contacting the fluoroperhalocarbon liquid with a body of particles comprising particles selected from the group consisting of alumina, alkali metal oxide, alkali metal hydroxide, alkaline earth oxide, alkaline earth hydroxide, silicon oxide, tin oxide, zinc oxide, alkaline earth basic carbonate and alkaline earth basic phosphate particles and mixtures thereof, and (b) separating the fluoroperhalocarbon liquid from the body of particles to recover the purified fluoroperhalocarbon liquid.

* * * * *

UNITED STATES PATENT AND TRADEMARK OFFICE
CERTIFICATE OF CORRECTION

PATENT NO. : 5,300,714
DATED : April 5, 1994
INVENTOR(S) : Pothapragada et al.

It is certified that error appears in the above-indentified patent and that said Letters Patent is hereby corrected as shown below:

Col. 1, lines 27 to 28, "material,".
should be --material.--.

Signed and Sealed this

Fourth Day of July, 1995

Attest:

BRUCE LEHMAN

*Attesting Officer*  *Commissioner of Patents and Trademarks*